US006992189B2

(12) United States Patent
Leong et al.

(10) Patent No.: US 6,992,189 B2
(45) Date of Patent: Jan. 31, 2006

(54) SYNTHESIS OF PIPERIDINE AND PIPERAZINE COMPOUNDS AS CCR5 ANTAGONISTS

(75) Inventors: William Leong, Westfield, NJ (US); Minzhang Chen, Plainsboro, NJ (US); Bosco A. D'sa, Edison, NJ (US); Man Zhu, Clark, NJ (US); Tong Xiao, Edison, NJ (US); Xiongwei Shi, Edison, NJ (US); Suhan Tang, Plainsboro, NJ (US); Dinesh Gala, East Brunswick, NJ (US); Andrew J. Goodman, Annandale, NJ (US); Christopher M. Nielsen, Westfield, NJ (US); Gary M. Lee, Belmont, CA (US); Juan A. Gamboa, New York, NY (US); Andrew D. Jones, Lexington, MA (US)

(73) Assignee: Schering Corporation, Kenilworth, NJ (US)

( * ) Notice: Subject to any disclaimer, the term of this patent is extended or adjusted under 35 U.S.C. 154(b) by 173 days.

(21) Appl. No.: 10/401,070

(22) Filed: Mar. 27, 2003

(65) Prior Publication Data

US 2004/0024217 A1 Feb. 5, 2004

Related U.S. Application Data

(60) Provisional application No. 60/368,749, filed on Mar. 29, 2002.

(51) Int. Cl.
*C07D 403/14* (2006.01)

(52) U.S. Cl. ...................... 544/295; 544/229; 544/360; 544/364; 514/252.18; 514/253.01; 514/253.11; 514/253.1; 514/253.09

(58) Field of Classification Search ............ 514/252.18, 514/253.01, 253.11, 253.1, 253.09; 544/295, 544/229, 360, 364
See application file for complete search history.

(56) References Cited

U.S. PATENT DOCUMENTS 6,391,865 B1 * 5/2002 Baroudy et al. .............. 514/63
2003/0144510 A1 * 7/2003 Gala et al. .................. 544/295

FOREIGN PATENT DOCUMENTS

| WO | WO 00/66559 | 8/2002 |
|---|---|---|
| WO | WO 02/66558 | 8/2002 |
| WO | WO 03/33490 | 4/2003 |

OTHER PUBLICATIONS

A. Palani et al., "Discovery of 4-[(Z)-4Bromophenyl)-(ethoxyimino)methyl]-1'-[(2, 4-dimethyl-3-pyridinyl)carbonyl]-4'-methyl-1,4'bipiperidine N-Oxide (SCH 351125): An Orally Bioavailable Human CCR5 Antagonist for the Treatment of HIV Infection", *J. Med. Chem.*, 44(21): 339-3342 (2001).

R. de Weerd et al., "A New Class of Chiral Detergents. The Formation of Single Micelles from N.N-Dimethyl-1-dodecyl-2, 4-dimethyl-3-carbamoylpyridinium Bromide. A CD Study", *J. Org. Chem.*, 49: 3413-3415 (1984).

T. J. Kress, "Synthesis and Proton NMR Spectra of the Monomethyl- and Dimethylpyrimidine-5-Carboxylic Acids. Regioselective Covalent Hydration at the 2- and 4- Ring Positions", *Heterocycles* 38(6): 1375-1382 (1994).

* cited by examiner

*Primary Examiner*—Celia Chang
(74) *Attorney, Agent, or Firm*—Palaiyur S. Kalyanaraman

(57) ABSTRACT

In its several embodiments, this invention discloses novel processes to prepare the compounds of formula II and formula IV:

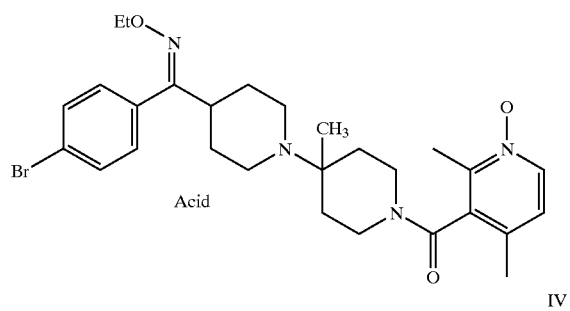

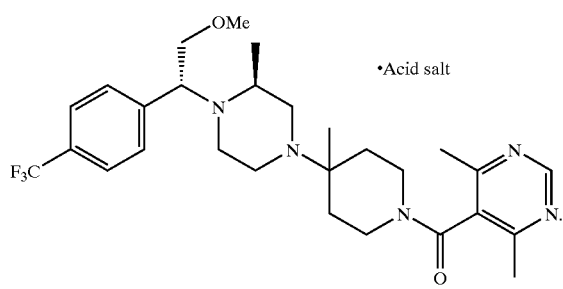

14 Claims, No Drawings

SYNTHESIS OF PIPERIDINE AND PIPERAZINE COMPOUNDS AS CCR5 ANTAGONISTS

FIELD OF THE INVENTION

This application claims priority from U.S. provisional patent application, Ser. No. 60/368,749, filed Mar. 29, 2002. This application discloses a novel process to synthesize certain substituted piperidines and piperazines useful as CCR5 receptor antagonists.

BACKGROUND OF THE INVENTION

Antagonists of the CCR5 receptor are useful for the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

WO 00/66559, published Nov. 9, 2000, discloses the piperidine compound of formula I, 4-[(Z)-(4-bromophenyl)(ethoxyimino)methyl]-1'-[(2,4-dimethyl-1-oxido-3-pyridinyl)carbonyl]-4'-methyl-1,4'-bipiperidine, its acid salt (the compound of formula II) and pharmaceutical compositions comprising I and II:

The compounds of formulas I and II are antagonists of the CCR5 receptor and are useful for the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease. Pending patent application Ser. No. 10/629,822 filed Oct. 11, 2002, which is incorporated herein by reference, discloses a novel process to synthesize the compound of formula I.

The piperazine compound of formula III, Piperidine, 4-[4-[(1R)-[4-(trifluoromethyl)phenyl]-2-methoxyethyl]-(3S)-methyl-1-piperazinyl]-4-methyl-1-[(4,6-dimethyl-5-pyrimidinyl)carbonyl, its acid salt (formula IV), and pharmaceutical compositions comprising the compounds of formulas III and IV are disclosed in WO 00/66558 published Nov. 9, 2000. The piperazine of formula III (a free-base) and its acid salt (formula IV) are disclosed therein as being useful as antagonists of CCR5 receptor.

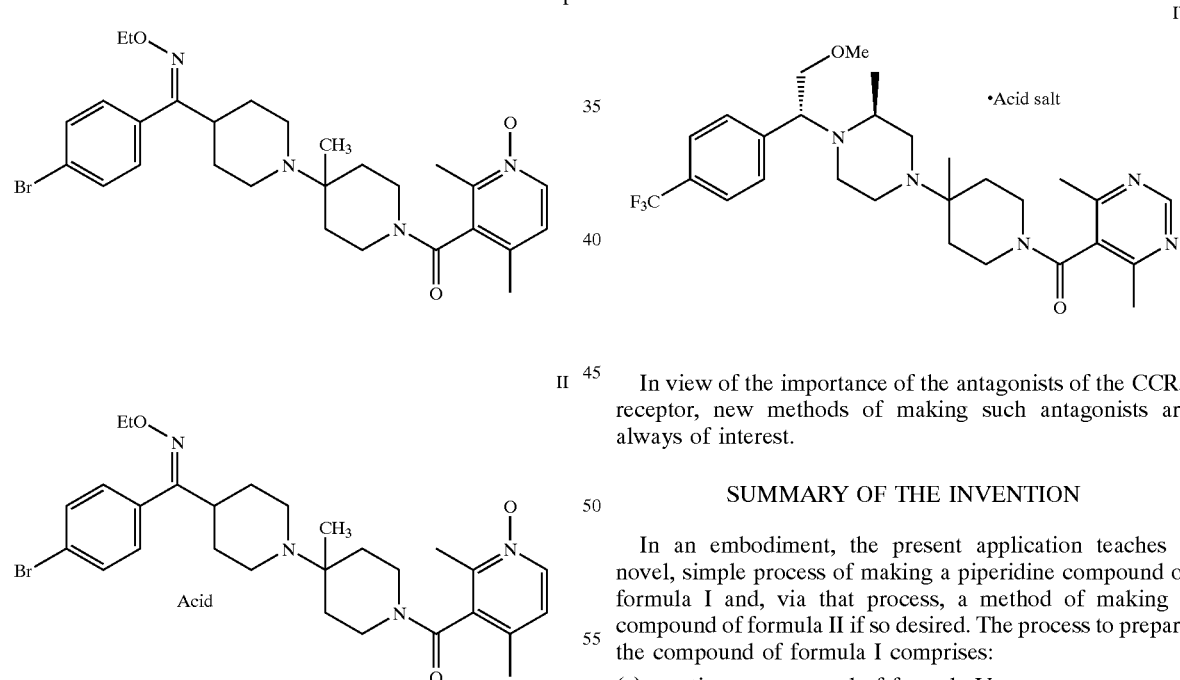

In view of the importance of the antagonists of the CCR5 receptor, new methods of making such antagonists are always of interest.

SUMMARY OF THE INVENTION

In an embodiment, the present application teaches a novel, simple process of making a piperidine compound of formula I and, via that process, a method of making a compound of formula II if so desired. The process to prepare the compound of formula I comprises:

(a) reacting a compound of formula V:

with a base to liberate the free base of the formula VI:

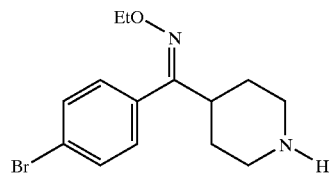

VI (b) reacting the compound of formula VI with the compound of formula VII

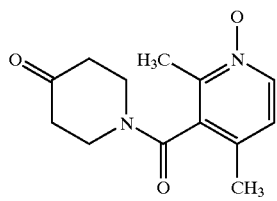

VII and a cyanating compound, to prepare the compound of formula VIII:

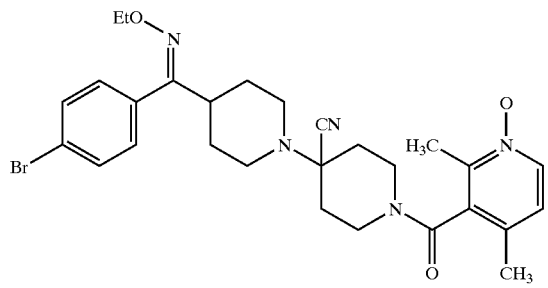

VIII and (c) reacting the compound of formula VIII with a methyl-metal and an organometallic reagent to yield the compound of formula I.

In another embodiment, this invention discloses a process to prepare the piperazine compound of formula III from a compound of formula X:

X said process comprising (a) reacting the compound of formula X with the compound of formula XI:

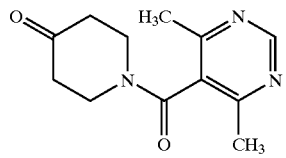

XI and a cyanating compound to form the compound of formula XII:

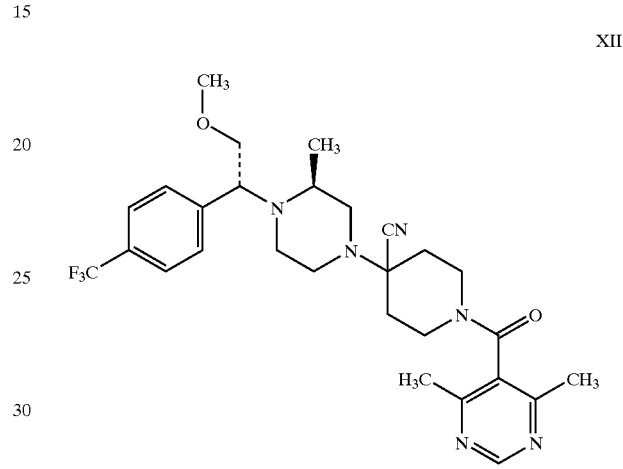

XII and (b) reacting said compound of formula XII with a methyl-metal and an organometallic reagent to yield a compound of formula III.

The inventive process to make the compounds of formulas I and III is economical and can be easily scaled-up.

DESCRIPTION OF THE INVENTION

In one embodiment, the present invention discloses a novel, easy-to-use process for preparing the compound of formula I, which may later be converted to the acid salt of formula II, if so desired. The inventive process is schematically described in Scheme 1:

Scheme I

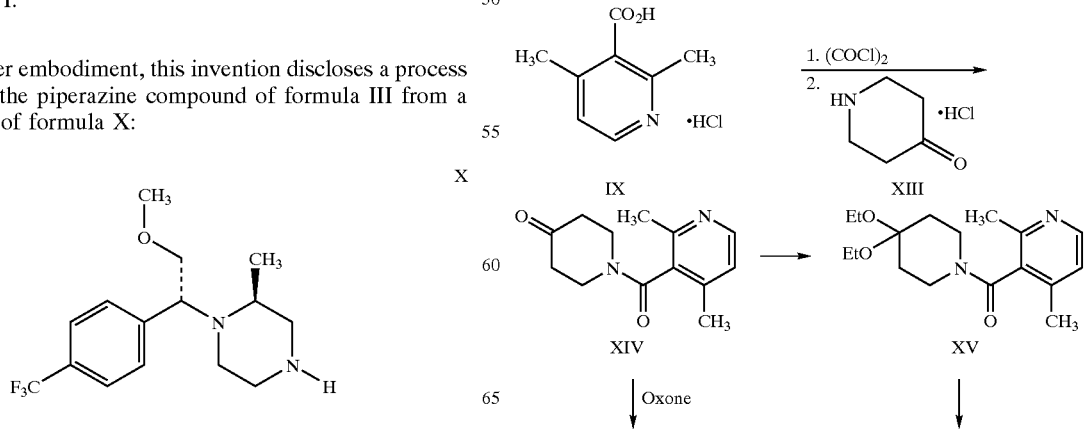

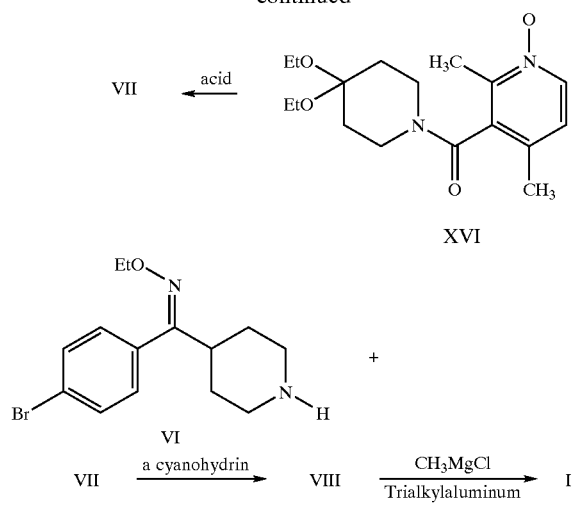

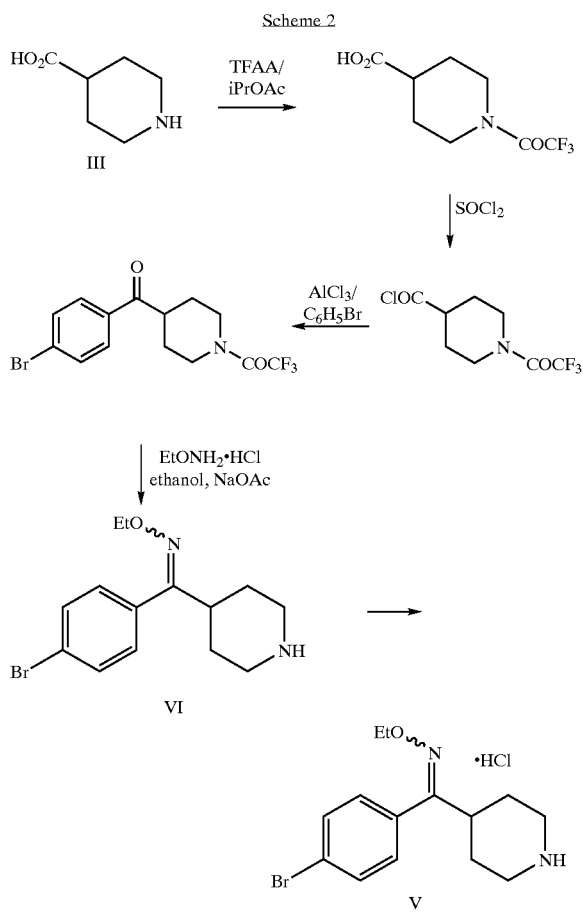

The preparation of the compounds of formulas V and VI is described in pending patent application Ser. No. 10/269,803, filed Oct. 11, 2002. An illustrative procedure to prepare the compounds of formula V and VI is shown in Scheme 2:

The various reaction steps outlined in the inventive processes of this application may additionally optionally contain one or more suitable solvents to facilitate the reaction. While the preferred reagents and reaction conditions for the various steps are described in detail in the Examples section, the following summarizes the details.

Isonipecotic acid is N-protected using trifluoroacetic anhydride in isopropyl acetate. The N-protected compound is converted to its acid chloride and the acid chloride is subjected to a Friedel-Crafts reaction with bromobenzene in the presence of aluminum chloride catalyst. The product is then converted to the ethyloxime by reacting with ethoxyamine hydrochloride. The ethyloxime is then deprotected in a base to form the compound of formula VI, which is then reacted with HCl to form the hydrochloride salt of formula V.

The compound of formula VII may be prepared as follows. 2,4-Dimethylnicotinic acid hydrochloride (CAS Registry number 133897-06-0; the acid cited in R. J. E. M. De Weerd et al, *J. Org. Chem.*(1984), 49, 3413–15) is converted to its acid chloride by reacting with a suitable reagent such as, for example, thionyl chloride, oxalyl chloride, methanesulfonyl chloride, toluenesulfonyl chloride, pivalyl anhydride, and diethyl chlorophosphite. A coupling agent may be employed. Non-limiting examples of suitable coupling agents include ethyl chloroformate; isobutyl chloroformate; diethyl chlorophosphonate; diethyl cyanophosphite; 1,1-carbonyldiimidazole; N,N-dicyclohexylcarbodiimide (DCC); (7-azabenzotriazol-1-yl) oxytris(dimethylamonino)phosphonium hexafluorophosphate ("AOP"); benzotriazol-1-yloxytris (dimethylamino)phosphonium hexafluorophosphate ("BOP"); bis(2-oxo-3-oxazolidinyl)phosphinic chloride ("BOP-Cl"); bromotris(dimethylamino)phosphonium hexafluorophosphate ("BroP"); bis(tetramethylenefluoroformamidinium)hexaflurophosphate ("BTFFH"); 2-chloro-1,3-dimethylimidazolidinium hexafluorophosphate ("CIP"); diphenylphosphinic chloride ("DppCl"); O-(7-azabenzotriazol-1-yl)-1,3-dimethyl-1,3-trimethyleneuronium hexafluorophosphate ("HAMTU"); O-(7-azabenzotriazol-1-yl)1,1,3,3-bis(tetramethylene) uronium hexafluorophosphate ("HAPipU"); S-(7-azabenzotriazol-1-yl)-1,1,3,3-bis(tetramethylene) thiouronium hexafluorophosphate ("HAPyTU"); O-(7-azabenzotriazol-1-yl)-1,1,3,3-bis(tetramethylene)uronium hexafluorophosphate ("HAPyU"); O-(7-azabenzotriazol-1-yl)-1,1,3,3-tetramethyluronium hexafluorophosphate ("HATU"); O-(benzotriazol-1-yl)-1,1,3,3-bis (pentamethylene)uronium hexafluorophosphate ("HBPipU"); O-(benzotriazol-1-yl)-1,1,3,3(tetramethylene) uronium hexafluorophosphate ("HBPyU"); O-(benzotriazolyl-1-yl)-1,1,3,3-tetramethyluronium hexafluorophosphate ("HBTU"); S-(1-Oxido-2-pyridinyl)-1,1,3,3-tetramethylthiouronium hexafluorophosphate ("HOTT"); (7-azabenzotriazol-1-yl-)oxytris(pyrrolidino) phosphonium hexafluorophosphate ("PyAOP"); benzotriazol-1-yloxy-tripyrrolidinophosphonium hexafluorophosphate ("PyBOP"); bromotripyrrolidinophosphonium hexafluorophosphate ("PyBrOP"); chlorotripyrrolidinophosphonium hexafluorophosphate ("PyClOP"); chloro-1,1,3,3-bis(tetramethylene)formamidinium hexafluorophosphate ("PyClU"); propanephosphoric anhydride ("PPA"); O-(benzotriazol-1-yl)-1,1,3,3-tetramethyluronium tetrafluoroborate ("TBTU"); O-(3,4-dihydro-4-oxo-1,2,3-benzotriazin-3-yl)1,1,3,3-tetramethyluronium tetrafluoroborate ("TDBTU"); tetramethylfluoroformamidinium hexafluorophosphate ("TFFH"); S-(1-oxido-2-pyrodinyl)-1,1,3,3-tetramethylthiouronium hexafluorophosphate ("TOTT"); and 1-ethyl-3-(3-dimethylaminopropyl)-carbodiimide ("EDCl") hydrochloride salt with or without 1-hydroxybenzotriazole hydrate ("HOBT"), and the like. A solvent may be employed for this reaction and a base catalyst is used. Non-limiting examples of suitable solvents include solvents such as, for example, ketone, nitrile, ester, ether, hydrocarbon and the like, and mixtures thereof. Non-limiting examples of suitable solvents further include tetrahydrofuran, toluene, acetonitrile, ethyl acetate, methyl ethyl ketone, dichloromethane and the like. Preferred solvent is acetonitrile. Non-limiting examples of suitable catalysts include amides such as N,N-dimethylformamide, N,N-dimethylacetamide and the like.

The reagent (for example, oxalyl chloride) is used generally in about 0.9 to about 5.0 molar equivalents with respect to 2,4-dimethyl nicotinic acid hydrochloride, preferably in about 1.0 to about 2.0 molar equivalents and typically in about 1.1 to about 1.2 molar equivalents. The solvent may be used generally in about 3 to 20 volume equivalents with respect to 2,4-dimethyl nicotinic acid hydrochloride, preferably in about 5 to 10 volume equivalents and typically in about 6 to 7 volume equivalents. The catalyst may be used generally in about 0.001 to about 0.5 molar equivalents with respect to 2,4-dimethyl nicotinic acid hydrochloride, preferably in about 0.005 to about 0.1 molar equivalents and typically in about 0.009 to about 0.01 molar equivalents. The acid may be dissolved, suspended or otherwise suitably dispersed in the solvent, the catalyst may be added, followed by a suitable reagent, e.g. oxalyl chloride. Temperature of the reaction may generally be about −10° C. to about 30° C., preferably about −5° C. to about 20° C. and typically about 0° C. to about 10° C. The product may be isolated by removing the solvent.

The so obtained product may be reacted directly (without purification) with 4-piperidone hydrochloride monohydrate (available from Aldrich Chemical Company, Milwaukee, Wis.) in a solvent such as, for example, ketone, nitrile, ester, ether, hydrocarbon and the like, and mixtures thereof. Acetonitrile is preferred. A base such as, for example, a trialkylamine (e.g. triethylamine, diisopropylethylamine, 1,4-diazabicyclo[2,2,2]octane, 1,8-diazabicyclo[5.4.0]undec-7-ene, tetramethyl ethylene diamine("TMEDA"), and the like), or an inorganic base (potassium carbonate, sodium carbonate, sodium bicarbonate, potassium bicarbonate etc) may be added. The 4-piperidone hydrochloride monohydrate may be used generally in about 0.9 to about 10.0 molar equivalents with respect to the product of the previous step, preferably in about 1.0 to about 2.0 molar equivalents and typically in about 1.0 to about 1.1 molar equivalents. The solvent may be used generally in about 5 to 30 volume equivalents with respect to the same product of the previous step, preferably in about 7 to 15 volume equivalents and typically in about 10 to 12 volume equivalents. The base may be used generally in about 0.9 to about 10 molar equivalents with respect to the product of the previous step, preferably in about 2.0 to about 4.0 molar equivalents and typically in about 3.0 to about 3.1 molar equivalents. The reaction may be carried out at temperatures generally in the range of about 20° C. to about 100° C., preferably about 30° C. to about 90° C. and typically about 60° C. to about 100° C. The product of formula XIV may be isolated by removal of the solvent and then used in the next step.

The compound of formula XIV may be reacted with triethylorthoformate, $CH(OC_2H_5)_3$ (available from Aldrich Chemical Company, Milwaukee, Wis.) in a suitable solvent, generally in the presence of an acid catalyst. Non-limiting examples of suitable solvents include ketone, nitrile, ester, ether, alcohol, hydrocarbon and the like, and mixtures thereof. Acetonitrile/ethanol mixture is preferred. $CH(OC_2H_5)_3$ may be used generally in about 0.9 to about 5.0 molar equivalents with respect to the compound of formula XIV, preferably in about 1.3 to about 2.5 molar equivalents and typically in about 1.5 to about 1.8 molar equivalents. The solvent ratio between acetonitrile and ethanol may be used generally in about 1:1 to 1:10, preferably in about 1:1.5 to 1:3 and typically in about 1:19 to 1:2.1. The volume of solvents may be used generally in about 2.0 to 10.0 volume equivalents with respect to the compound of formula XIV, preferably in about 2.0 to 5.0 volume equivalents and typically in about 2.5 to 3.5 volume equivalents. The acid catalyst may be used generally in about 0.1 to about 0.8 molar equivalents with respect to the compound of formula XIV, preferably in about 0.15 to about 0.4 molar equivalents and typically in about 0.2 to about 0.25 molar equivalents. The reaction may be carried out at temperatures generally in the range of about 0° C. to about 100° C., preferably about 70° C. to about 100° C. and typically about 80° C. to 95° C. The product of formula XV may be isolated by removal of the solvent and then used in the next step.

The compound of formula XV may then be oxidized to the N-oxide by known N-oxidation procedures. Generally, a peroxide such as, for example, $H_2O_2$ or an inorganic or organic peroxide, or complexes and adducts containing such peroxides or peroxy compounds, peracids, other oxidizing agents and the like may be used. Non-limiting examples of suitable oxidizing agents include m-chloroperbenzoic acid; phthalic anhydride/urea-$H_2O_2$; KMnO4; oxone; ozone; inorganic peracids; peracetic acid; $Na_2WO_4$; a mixture of benzonitrile, $H_2O_2$ and methanol; a mixture of trifluoroacetic acid, $H_2O_2$ and $H_2SO_4$ and the like. In a general procedure, a mixture of a compound such as phthalic anhydride, urea-$H_2O_2$ and the compound of formula VIII may be dissolved, or dispersed or suspended in an appropriate solvent such as, for example, a $C_3$–$C_9$ alkanone, a $C_4$–$C_{10}$ cycloalkanone, a $C_5$–$C_{12}$ alkyl ether, 1,2-dimethoxyethane, 1,2-diethoxyethane, acetonitrile, benzonitrile, diglyme, tetrahydrofuran, 1,4-dioxan, benzene, toluene, xylene, chlorobenzene, dichlorobenzene, acetonitrile, dimethyl sulphoxide, sulpholane and the like and mixtures thereof, preferably a ketone such as methyl ethyl ketone or a nitrile such as acetonitrile, and more preferably acetonitrile. The reaction may be carried out at temperatures generally in the range of about −10° C. to about 40° C., preferably about −5° C. to about 10° C. and typically about −5° C. to about 5° C. The phthalic anhydride may be used generally in about 0.9 to 5 molar equivalents, preferably in about 1 to 3 molar equivalents and typically in about 1–1.5 molar equivalents, with respect to the compound of formula VIII. The urea-hydrogen peroxide is generally used in about 0.9 to 8 molar equivalents, preferably in about 1 to 4 molar equivalents and typically in about 2–3 molar equivalents. The product of formula XVI may be isolated by customary procedures well known to those skilled in the art.

Alternatively, compound XIV may be directly oxidized to VII using known N-oxidation procedures. Generally, a peroxide such as, for example, $H_2O_2$ or an inorganic or organic peroxide, or complexes and adducts containing such peroxides or peroxy compounds, peracids, other oxidizing agents and the like may be used. Non-limiting examples of suitable of suitable oxidizing agents include m-chloroperbenzoic acid; phthalic anhydride/urea-$H_2O_2$; KMnO4; oxone; ozone; inorganic peracids; peracetic acid; $Na_2WO_4$; a mixture of benzonitrile, $H_2O_2$ and methanol; a mixture of trifluoroacetic acid, $H_2O_2$ and $H_2SO_4$ and the like.

The compound of formula XVI may then be converted into the compound of formula VII by treatment with a suitable acid in a suitable solvent. Non-limiting examples of suitable solvents include nitrile, ether, hydrocarbon and the like, and mixtures thereof. Tetrahydrofuran is preferred. Non-limiting examples of suitable acids include p-toluenesulfonic acid, benzenesulfonic acid and the like. p-Toluenesulfonic acid is preferred. The acid may be used generally in about 0.01 to about 1.0 molar equivalents with respect to the compound of formula XIV, preferably in about 0.02 to about 0.5 molar equivalents and typically in about 0.05 to about 0.1 molar equivalents. The solvent may be used generally in about 2 to 20 volumes with respect to the compound of formula XIV, preferably in about 3 to 10 volumes and typically in about 3 to 5 volumes. The reaction may be carried out at temperatures generally in the range of about 0° C. to reflux, preferably about 50° C. to reflux and typically about 60° C. to 70° C. The product of formula VII may be isolated by methods known to those skilled in the art.

The compounds of formulas VI and VII may be reacted as follows to form the compound of formula I. If the compound of formula VI is available, it can be used. If the acid salt of formula V is available, the compound of formula VI may be generated in situ from the acid salt of formula V by treatment with a suitable base. Non-limiting examples of suitable bases include i) a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; or (ii) a metal salt of a $C_1$–$C_{12}$ alkanol, a $C_3$–$C_{12}$ cycloalkanol, a ($C_3$–$C_8$ cycloalkyl)$C_1$–$C_6$ alkanol; ammonia; a $C_1$–$C_{12}$ alkylamine; a di($C_1$–$C_{12}$ alkyl)amine; a $C_3$–$C_8$ cycloalkylamine; a N—($C_3$–$C_8$ cycloalkyl)-N—($C_1$–$C_{12}$ alkyl)amine; a di($C_3$–$C_8$ cycloalkyl)amine; a ($C_3$–$C_8$ cycloalkyl)$C_1$–$C_6$ alkylamine; a N—($C_3$–$C_8$-cycloalkyl)$C_1$–$C_6$-alkyl-N—($C_1$–$C_{12}$ alkyl)amine; a N—($C_3$–$C_8$ cycloalkyl)$C_1$–$C_6$ alkyl-N—($C_3$–$C_8$ cycloalkyl)amine; a di[($C_1$–$C_6$ cycloalkyl)$C_1$–$C_6$ alkyl]amine; and a heterocyclic amine selected from the group consisting of imidazole, triazole, pyrrolidine, piperidine, heptamethyleneimine, morpholine, thiomorpholine and a 1-($C_1$–$C_4$ alkyl)piperazine, and mixtures thereof. Preferred basic compounds are KOH, NaOH, $Na_2CO_3$, $K_2CO_3$, $K_2CO_3$, $NaHCO_3$, $KHCO_3$, tetramethylguanidine, DBU (from Aldrich Chemical Company), diisopropylethylamine and mixtures thereof. A preferred base is a carbonate such as $Na_2CO_3$ or $K_2CO_3$, the latter being more preferred. The compounds of formulas VI, VII and a cyanating compound may be reacted in a suitable solvent to form the compound of formula VIII. Non-limiting examples of suitable cyanating compounds include HCN, acetone cyanohydrin; cyclohexanone cyanohydrin; a mixture of $(C_2H_5)_2AlCN$ and $Ti(OPr)_4$, a mixture of acetic acid, $H_2SO_4$; $NaHSO_4$, $KHSO_3$ or $Na_2S_2O_5$ and a cyanide source such as NaCN or KCN; trimethylsilylcyanide; glycolonitrile; mandelonitrile; glycinonitrile; acetone amino nitrile; and dimethylaminoacetonitrile. The cyanating compound is preferably acetone cyanohydrin or NaCN/acetic acid, and most preferably acetone cyanohydrin. Non-limiting examples of suitable solvents include ester, nitrile, ether, hydrocarbon and the like, and mixtures thereof. Ethyl acetate is preferred. The cyanating compound is used generally in about 0.9 to about 3 molar equivalents with respect to the compound of formula VI, preferably in about 1.1 to about 1.5 molar equivalents and typically in about 1.2 molar equivalents. The solvent may be used generally in about 5 to 20 volumes with respect to the compound of formula VI, preferably in about 8 to 12 volumes and typically in about 10 volumes.

Typically the reaction is carried out at about the reflux temperature of the solvent. Removal of the solvent yields the compound of formula VIII which may be isolated by methods well known to those skilled in the art.

The compound of formula VIII may then be converted to the compound of formula I as follows. The compound of formula VIII may be dissolved in a suitable solvent and then reacted with an organometallic reagent and a methyl-metal. Non-limiting examples of suitable organometallic reagents include, for example, trimethylaluminum, triethylaluminum, triethylborane, methyl zinc, tetramethyl tin and the like. Trimethylaluminum is preferred. Non-limiting examples of suitable methyl-metals include methyl magnesium chloride, methyl magnesium bromide, methyl magnesium iodide, methyl lithium and the like. Non-limiting examples of suitable solvents include ether (for example, a $C_5$–$C_{12}$ alkyl ether, 1,2-dimethoxyethane, 1.2-diethoxyethane, diglyme, 1,4-dioxane, tetrahydrofuran and the like), hydrocarbon such as, for example, toluene, xylene, chlorobenzene, dichlorobenzene and the like, or a mixture of a hydrocarbon listed above with an ether such as those listed above, nitrile, ester and the like. Tetrahydrofuran is preferred. The organometallic reagent (for example, a trialkylaluminum) is used generally in about 0.9 to about 6 molar equivalents with respect to the compound of formula VIII, preferably in about 2 to about 5 molar equivalents and typically in about 3.5 to about 4.5 molar equivalents. The solvent may be used generally in about 2 to 20 volumes with respect to the compound of formula VIII, preferably in about 3 to 10 volumes and typically in about 4 to 7 volumes. The methyl-metal may be used generally in about 0.9 to about 6 molar equivalents with respect to the compound of formula VIII, preferably in about 1 to about 4 molar equivalents and typically in about 1.5 to about 3 molar equivalents. The reaction may be carried out at temperatures generally in the range of about −10° C. to about 30° C., preferably about −10° C. to about 20° C. and typically about −5° C. to about 5° C. The product of formula I may be isolated by methods known to those skilled in the art.

The piperazine compound of formula III can be prepared from the compounds of formulas X and XI in a manner analogous to the above-described preparation of the piperidine compound of formula I from the compounds of formulas VI and VII. If the compound of formula X is available, it can be used. If the acid salt of the compound of formula X is available, then the compound of formula X may be generated in situ from that acid salt by treatment with a suitable base. Non-limiting examples of suitable bases include a metal hydroxide, oxide, carbonate or a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; or a metal salt of a $C_1$–$C_{12}$ alkanol, a $C_3$–$C_{12}$ cycloalkanol, a ($C_3$–$C_8$ cycloalkyl)$C_1$–$C_6$ alkanol; ammonia; a $C_1$–$C_{12}$ alkylamine; a di($C_1$–$C_{12}$ alkyl)amine; a $C_3$–$C_8$ cycloalkylamine; a N—($C_3$–$C_8$ cycloalkyl)-N—($C_1$–$C_{12}$ alkyl)amine; a di($C_3$–$C_8$ cycloalkyl)amine; a ($C_3$–$C_8$ cycloalkyl)$C_1$–$C_6$ alkylamine; a N—($C_3$–$C_8$-cycloalkyl)$C_1$–$C_6$-alkyl-N—($C_1$–$C_{12}$ alkyl)amine; a N—($C_3$–$C_8$ cycloalkyl)$C_1$–$C_6$ alkyl-N—($C_3$–$C_8$ cycloalkyl)amine; a di[($C_1$–$C_6$ cycloalkyl)$C_1$–$C_6$ alkyl]amine; and a heterocyclic amine selected from the group consisting of imidazole, triazole, pyrrolidine, piperidine, heptamethyleneimine, morpholine, thiomorpholine and a 1-($C_1$–$C_4$ alkyl)piperazine or mixtures thereof. Preferred basic compounds are KOH, NaOH, $Na_2CO_3$, K$_2$CO$_3$, K$_2$CO$_3$, NaHCO$_3$, KHCO$_3$, tetramethylguanidine, DBU, diisopropylethylamine and mixtures thereof. A more preferred base is a carbonate such as Na$_2$CO$_3$ or K$_2$CO$_3$, the latter being still more preferred. The compounds of formulas X, XI and a cyanating compound may be reacted in a suitable solvent to form the compound of formula XII. Non-limiting examples of suitable cyanating compounds include HCN; acetone cyanohydrin; cyclohexanone cyanohydrin; a mixture of (C$_2$H$_5$)$_2$AlCN and Ti(OPr)$_4$, a mixture of acetic acid, H$_2$SO$_4$; NaHSO$_4$, KHSO$_3$ or Na$_2$S$_2$O$_5$; NaCN, KCN, NaCN and acid; KCN and acid; trimethylsilylcyanide; glycolonitrile; mandelonitrile; glycinonitrile; acetone amino nitrile; dimethylaminoacetonitrile; and mixtures thereof. The cyanating compound is preferably acetone cyanohydrin or NaCN/acetic acid, and most preferably NaCN/acetic acid. Non-limiting examples of suitable solvents include ester, nitrile, ether, hydrocarbon and the like, and mixtures thereof. Isopropyl acetate is preferred. The cyanating compound is used generally in about 0.9 to about 10 molar equivalents with respect to the acid salt of compound of formula X, preferably in about 1 to about 4 molar equivalents and typically in about 1.5 to about 2.5 molar equivalents. The solvent may be used generally in about 5 to 20 volume equivalents with respect to the acid salt of compound of formula X, preferably in about 5 to 10 volume equivalents and typically in about 7 to 8 volume equivalents. The base may be used generally in about 1 to about 10 molar equivalents with respect to the acid salt of compound of formula X, preferably in about 1 to about 4 molar equivalents and typically in about 1.5 to about 2 molar equivalents. Typically the reaction is carried out at about the reflux temperature of the solvent. Removal of the solvent yields the compound of formula XII which may be isolated by methods well known to those skilled in the art.

The compound of formula XII may then be converted to the compound of formula III as follows. The compound of formula XII may be dissolved in a suitable solvent and then reacted with a methyl-metal with or without an organometallic reagent. If an organometallic reagent is used, non-limiting examples of suitable organometallic reagents include trimethylaluminum, triethylaluminum, triethylborane, methyl zinc, tetramethyl tin and the like. Trimethylaluminum is preferred. Non-limiting examples of suitable methyl-metals include methyl magnesium chloride, methyl magnesium bromide, methyl magnesium iodide, methyl lithium and the like. Non-limiting examples of suitable solvents include ether (for example, a C$_5$–C$_{12}$ alkyl ether, 1,2-dimethoxyethane, 1.2-diethoxyethane, diglyme, 1,4-dioxane, tetrahydrofuran and the like), hydrocarbon solvent such as, for example, toluene, xylene, chlorobenzene, dichlorobenzene and the like, or a mixture of a hydrocarbon listed above with an ether such as those listed above, nitrile, ester and the like. Tetrahydrofuran is preferred. The organometallic reagent is used generally in about 0 to about 10 molar equivalents with respect to the compound of formula XII, preferably in about 1 to about 5 molar equivalents and typically in about 1.8 to about 2.5 molar equivalents. The solvent may be used generally in about 1 to 20 volume equivalents with respect to the compound of formula XII, preferably in about 10.0 equivalents and typically in about 5.0 equivalents. The methyl-metal may be used generally in about 0.9 to about 10 molar equivalents with respect to the compound of formula XII, preferably in about 1 to about 4 molar equivalents and typically in about 2.5 to about 3.0 molar equivalents. The reaction may be carried out at temperatures generally in the range of about −10° C. to about 40° C., preferably about 10° C. to about 35° C. and typically about 20° C. to about 30° C. The product of formula III may be isolated by methods known to those skilled in the art.

The preparation of the compound of formula X is disclosed in co-pending provisional patent application, Ser. No. 10/400,429, filed of even date herewith. An illustrative process to prepare the compound of formula X is shown in Scheme 3:

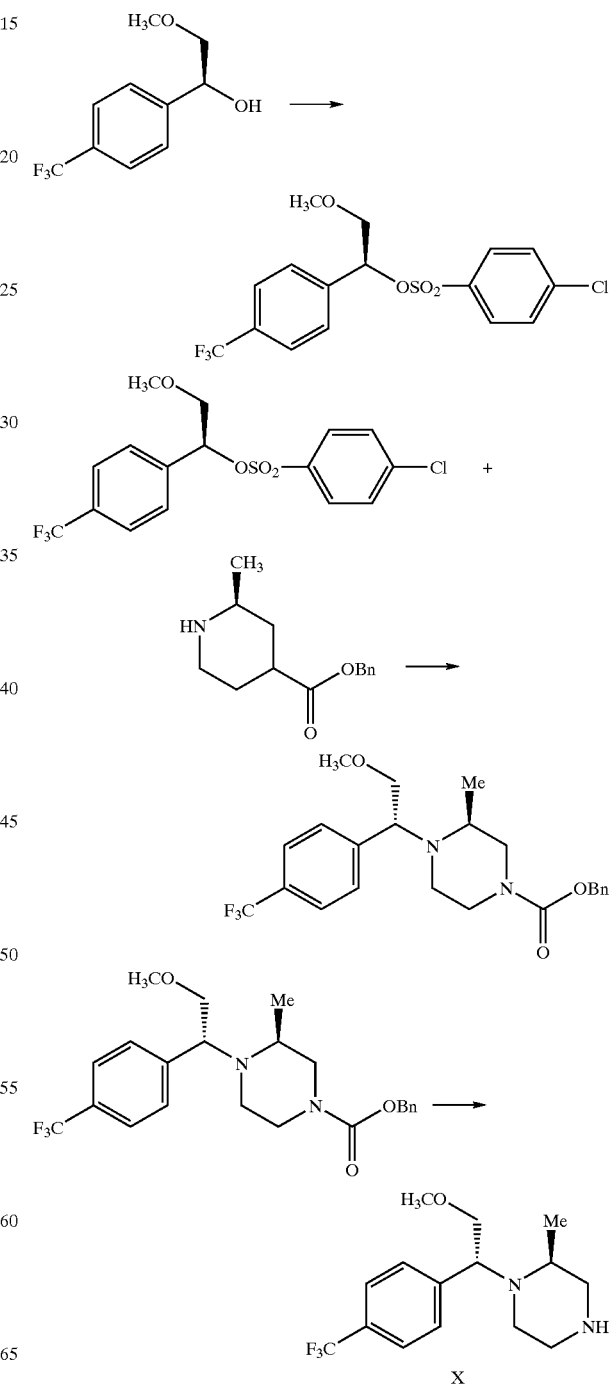

The experimental details for Scheme 3 are illustrated in the EXAMPLES section.

The compound of formula XI may be prepared from pyrimidine-2,4-dimethyl-5-carboxylic acid which acid is disclosed by T. Kress, *Heterocycles* (1994), 38(6), 1375–82. Pyrimidine-2,4-dimethyl-5-carboxylic acid may be dissolved, suspended or otherwise suitably dispersed in a suitable solvent and reacted with 4-piperidone monohydrate hydrochloride in the presence of a suitable sulfonyl chloride and a base. Non-limiting examples of suitable solvents include ketone, nitrile, ester, ether, hydrocarbon and the like, and mixtures thereof. Acetonitrile is preferred. Non-limiting examples of suitable sulfonyl chlorides include methane sulfonyl chloride, benzene sulfonyl chloride, toluenesulfonyl chloride and the like. Non-limiting examples of suitable bases include N,N,N',N'-tetramethyl ethylenediamine ("TMEDA", from Aldrich Chemical Company), tetramethylguanidine, DBU, diisopropylethylamine, triethylamine and mixtures thereof. The sulfonyl chloride is used generally in about 0.9 to about 5 molar equivalents with respect to the pyrimidine-2,4-dimethyl-5-carboxylic acid, preferably in about 2 to about 3 molar equivalents and typically in about 2.0 to about 2.1 molar equivalents. The solvent may be used generally in about 2 to 20 volumes with respect to the pyrimidine-2,4-dimethyl-5-carboxylic acid, preferably in about 1 to 15 volumes and typically in about 10 volumes. The base may be used generally in about 0.9 to about 10 molar equivalents with respect to the pyrimidine-2,4-dimethyl-5-carboxylic acid, preferably in about 2 to about 5 molar equivalents and typically in about 3 to about 3.5 molar equivalents. The reaction may be carried out at temperatures generally in the range of about −20° C. to about 30° C., preferably about −15° C. to about 20° C. and typically about −15° C. to 5° C. The product of formula XI may be isolated by removal of the solvent or other such methods known to those skilled in the art.

The compounds of formulas X and XI may be reacted, along with a suitable cyanating compound, similar to the preparation of the compound of formula VIII described above, to prepare the compound of formula III.

If desired, the compounds of formulas I and III may be further converted to their respective acid salts of formulas II and IV by suitable procedures well known to those skilled in the art. As stated above, the compounds of formulas II and IV are known as having utility as CCR5 antagonists. Additionally, they may also be formulated into pharmaceutical compositions for administration to a patient in need thereof. Thus, the present invention offers a simple economical way of preparing such CCR5 antagonists and pharmaceutical compositions.

The products of the various steps in the reaction schemes described herein may be isolated and purified by conventional techniques such as, for example, filtration, recrystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following nonlimiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:
HPLC=High Performance Liquid Chromatography
M.pt: melting point
NMR=nuclear magnetic resonance spectroscopy
DMSO=dimethylsulfoxide
IPrOAc=isopropyl acetate
TBME, MTBE=t-butyl methyl ether
THF=tetrahydrofuran
HOAc=Acetic acid
EtOAc=Ethyl acetate
IPA=isopropanol
IPOAc=isopropyl acetate
DMF=N,N-dimethylformamide
DBU=1,8-Diazabicyclo[5.4.0]-undec-7-ene
KF=Karl Fischer
HOBT=1-hydroxybenzotriazole hydrate
EDCl.HCl=1-(3-dimethylaminopropyl)-3-ethylcarbodiimide hydrochloride
mL=milliliters
g=grams
rt=room temperature (ambient)
Boc (or t-Boc)=tert-butoxycarbonyl 1. Preparation of the Compound of Formula I:

Example 1

Conversion of the Compound of Formula IX to the Compound of Formula XIV

To a slurry of 262 g of 2,4-dimethylnicotinic acid hydrochloride (Formula IX) in 1.8 L of acetonitrile at 0° C., catalytic amount of DMF (1 mL) was added followed by 147 mL of oxalyl chloride while the temperature was controlled to below 10° C. during the addition. The resulting slurry was warmed to 25° C. and stirred for 2 hours. After vacuum concentration to remove 500 mL of solvent, the resulting slurry was added to a slurry of 215 g of 4-piperidone hydrochloride monohydrate (Formula XIII) in 700 mL of acetonitrile in the presence of 588 mL of $Et_3N$ at 0° C. The resulting slurry was heated to 45–50° C. for 6 hours followed by 75–80° C. for 3 hours. After cooling to 0° C. for 2 hours, the solid was filtered off and washed by 500 mL of acetonitrile. Removal of solvent then gave the desired compound of formula XIV in 85–90% yield as an oil.

$^1$H NMR (500 MHz, $CDCl_3$) □□□8.35 (d, J=5.2 Hz, 1H), 6.98 (d, J=5.2 Hz, 1H), 4.07 (m, 2H), 3.45 (m, 2H), 2.56 (m, 2H), 2.46 (s, 3H), 2.34 (m, 2H), 2.24 (s, 3H);

$^{13}$C NMR (125 MHz, $CDCl_3$) □□205.6, 168.0, 153.6, 149.0, 143.4, 130.9, 122.6, 44.7, 41.2, 40.7, 40.3, 22.2, 18.7;

MS (Cl) m/z 233 ($M^+$+H), 232 ($M^+$)

HRMS calcd for $C_{13}H_{17}N_2O_2$: 233.1290 (M$^+$+H), Found: 233.1299.

Example 2

Preparation of the Compound of Formula XV

To a solution of the oil from Example 1 in 260 mL acetonitrile and 520 mL of EtOH, toluenesulfonic acid monohydrate (65.5 g) was added followed by 354 mL of HC(OEt)$_3$. The solution was then heated to reflux for 6 hours. After cooling to 20–30° C., the solution was quenched into a solution of 147 g of Na$_2$CO$_3$ and 52 g of NaCl in 1.6L of H$_2$O. After vacuum concentration to remove 700 mL of solvent, the resulting solution was extracted with 500 mL THF and 1L of EtOAc. The separated organic layer was then washed with 500 mL of 5% NaCl solution. Removal of solvent then gave the desired compound of formula XV in 85–90% yield (over two steps of Examples 1 and 2 combined) as an oil.

$^1$H NMR (500 MHz, CDCl$_3$) □□□8.34 (d, J=5.1 Hz, 1H), 6.97 (d, J=5.1 Hz, 1H), 3.83 (t, J=5.9 Hz, 2H), 3.45 (m, 4H), 3.17 (m, 2H), 2.46 (s, 3H), 2.24 (s, 3H), 1.85 (m, 2H), 1.65 (m, 2H), 1.17 (m, 6H)

$^{13}$C NMR (125 MHz, CDCl$_3$) □□167.5, 153.7, 148.7, 143.4, 131.8, 122.6, 98.0, 55.4, 43.4, 38.3, 34.3, 33.3, 22.2, 18.7, 15.3;

MS (CI) m/z 307 (M$^+$+H)

HRMS calcd for $C_{17}H_{27}N_2O_3$: 307.2022 (M$^+$+H), Found: 307.2021.

Example 3

Preparation of the Compound of Formula XVI

To a slurry of 252 g of phthalic anhydride and 246 g of Urea Hydrogen peroxide in 400 mL of acetonitrile at 0° C., a solution of 400 g of the compound of formula XV in 400 mL acetonitrile was added while the temperature was controlled to below 5° C. The solution was then stirred at 5° C. for 16 hours. The reaction was quenched by adding a solution of 180 g of Na$_2$SO$_3$ in 1.2L H$_2$O while the temperature was controlled to below 5° C. After stirring at 5° C. for half hour, the slurry was added into a solution of 240 g of Na$_2$CO$_3$ in 1.2 L of H$_2$O. The aqueous layer was then extracted with 800 mL of THF and 800 mL of EtOAc. The separated organic layer was washed with 800 mL of 10% NaCl solution. Removal of solvent followed by crystallization from 400 mL EtOAc and 200 mL of heptane gave the desired compound of formula XVI in ~80% yield.

$^1$H NMR (500 MHz, CDCl$_3$) δ 8.13 (d, J=6.7 Hz, 1H), 6.98 (d, J=6.7 Hz, 1H), 3.85 (m, 2H), 3.73 (m, 2H), 3.44 (m, 4H), 3.16 (t, J=6.4 Hz, 2H), 2.41 (s, 3H), 2.11 (s, 3H), 1.83 (m, 2H), 1.64 (m, 2H), 1.16 (m, 6H);

$^{13}$C NMR (125 MHz, CDCl$_3$) δ 164.7, 145.0, 138.3, 134.7, 132.6, 124.8, 97.8, 55.4, 43.5, 38.5, 34.2, 33.2, 18.3, 15.7, 15.1;

MS (CI) m/z 323 (M$^+$+H)

HRMS calcd for $C_{13}H_{17}N_2O_4$: 323.1971 (M$^+$+H), Found: 323.1969.

Example 4

Preparation of the Compound of Formula VII

To a solution of 100 g of the compound of formula XVI in 400 mL of THF at 20–30° C., was added 3.0 g of toluenesulfonic acid monohydrate and 8.4 mL of water. The solution was heated to reflux for 16 hours, cooled to 45–55° C., and treated with 2.2 mL of Et$_3$N. The mixture was dried azeotropically to a KF of less than 0.2% by distillation. The reaction was agitated at 15–20° C. for 6 hours and the mixture was filtered. The wet cake was dried under vacuum at 25–35° C. for 12 hours to give 57 g (71.4%) of the compound of formula VII as white solids.

$^1$H NMR (500 MHz, CDCl$_3$) δ 8.17 (d, J=6.7 Hz, 1H), 7.02 (d, J=6.7 Hz, 1H), 4.17 (m, 1H), 3.99 (m, 1H), 3.50 (m, 2H), 2.60 (m, 2H), 2.45 (s, 3H), 2.37 (m, 2H), 2.25 (s, 3H);

$^{13}$C NMR (125 MHz, CDCl$_3$) δ 204.9, 165.3, 145.0, 138.7, 133.9, 132.4, 125.1, 44.8, 41.0, 40.6, 18.3, 15.2;

MS (CI) m/z 249 (M$^+$+H)

HRMS calcd for $C_{13}H_{17}N_2O_3$: 249.1239 (M$^+$+H), Found: 249.1237.

Example 5

Alternate Method of Preparing the Compound of Formula VII

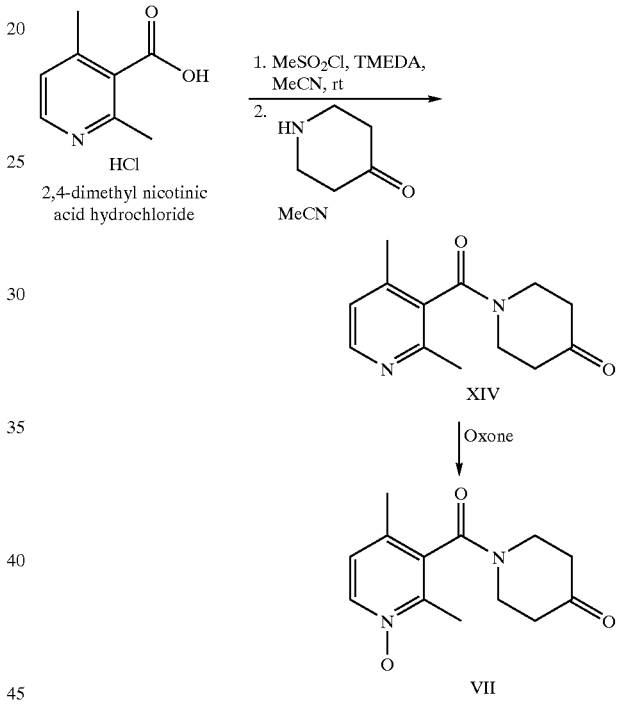

To a suspension of 2,4-dimethylnicotinic acid (10.0 g, 1.00 eq) and 4-piperidone monohydrate hydrochloride (8.2 g, 1.00 eq) in 100 mL of acetonitrile at 0° C. was added 12.0 mL (1.5 eq) of N,N,N,N-tetramethyl ethylenediamine (TMEDA). To this suspension was simultaneously added TMEDA (12.0 mL, 1.5 eq) and mesyl chloride (methanesulfonyl chloride) (8.0 mL, 1.9 eq) over 8 hours. Additional 4-piperidone monohydrate hydrochloride (1.2 g, 0.15 eq) was added to the suspension followed by the addition of TMEDA (2.4 mL, 0.3 eq) and mesyl chloride (1.3 mL, 0.3 eq) over 3 hours. To the suspension methane sulfonic acid (3.0 mL) was added to the batch to precipitate out the TMEDA salts. The batch was filtered and washed twice with 30 mL of acetonitrile. The filtrate was concentrated to 20 mL and then diluted with 40 mL TBME at reflux. The solution was cooled slowly to 0° C. over 4 hours to crystallize the compound of formula XIV in 70% yield.

To the compound of formula XIV (1 g) was added 2.5 ml H$_2$O. The mixture was cooled to 0–5° C. and added 5 g of a one to one mixture of oxone and Na$_3$PO$_4$.12H$_2$O. The mixture was then agitated for about one hour at 10–20° C. The mixture was filtered to remove inorganic salts. These salts were washed with 5 ml of n-butanol which was combined with the aqueous filtrate. The two phase solution was agitated and then partitioned. The aqueous layer was extracted with 5 ml of n-butanol. The combined n-butanol layers were concentrated to an oil. The oil was dissolved in 2 ml of THF at reflux. The solution was slowly cooled to about 0° C. Any solids that formed were collected and dried to afford about 0.5 g of compound VII.

Example 5A

A Second Alternate Method of Preparing the Compound of Formula VII

The compound of formula XIV may be directly oxidized to the compound of formula VII by the following procedure. To a slurry of 194 g of compound of formula XIV and 669 g of $KHCO_3$ in 250 mL of acetonitrile and 1L $H_2O$ at 10–15° C., 617 g of oxone was slowly added as solid. (Other bases like potassium carbonate, sodium carbonate, sodium bicarbonate, sodium phosphate, potassium phosphate, sodium hydroxide, potassium hydroxide and like, and other solvents such as ether, alcohol, ester, nitrile and like, can also be used in this reaction). After stirring the slurry for 10 minutes, the solid was filtered off. The filtrate was concentrated under vacuum to dryness followed by extracting the solid with 1L of hot acetonitrile to give the crude compound of formula VII in acetonitrile (after filtration). Removal of solvent followed by crystallization from 100 mL acetonitrile and 600 mL of THF gave the desired product (Formula VII) in ~70% yield.

Example 6

A Third Alternate Preparation of the Compound of Formula VII

The compound of formula VII was also prepared from the ester of 2,4-dimethylnicotinic acid by first converting it to the N-oxide and then coupling the N-oxide with 4-piperidone hydrochloride monohydrate as shown below:

Preparation of the N-oxide: The slurry of 3.3 kg of phthalic anhydride and 3.15 kg of urea hydrogen peroxide in 8 L of acetonitrile was heated to dissolve. The solution of 3 kg of the ethyl ester of 2,4-dimehtylnicotinic acid was added while the temperature was controlled below 40° C. After stirring at 40° C. for 3 hours, the solution was cooled to 0° C. Then, it was added into a solution of 2.1 kg of $Na_2SO_3$ and 4.6 kg of $K_2CO_3$ in 12 L of $H_2O$. The aqueous solution was extracted three times with EtOAc (5L each time). The combined organic layer was concentrated to give the desired N-oxide in 95% yield as an oil.

$^1$H NMR ($CDCl_3$, 400 MHz): δ 8.43 (d, J=5.3 Hz, 1H), 7.02 (d, J=5.3 Hz, 1H), 4.42 (q, J=7.1 Hz, 2H), 2.51 (s, 3H), 2.32 (s, 3H), 1.44 (t, J=7.1 Hz, 3H).

Hydrolysis to the Acid: To a solution of the above oil (ethyl ester) in 4.5L of THF at 20–30° C., a slurry of 1.05 kg of $LiOH.H_2O$ in 3.9L of $H_2O$ was added. The solution was heated to 40° C. and stirred for 2 hours. After cooling the solution to 20–30° C., the aqueous solution was extracted with 1.5L of TBME. The separated aqueous layer was then added 2.3 L of concentrated HCl. After cooling the slurry to 0° C. for 1 hour, the solid was filtered and dried under vacuum at 60° C. to give the desired acid (2.5 kg) in 89% yield over the combined above-noted two steps.

$^1$H NMR (DMSO, 400 MHz): δ 8.22 (d, J=6.6 Hz, 1H), 8.00 (d, J=6.6 Hz, 1H), 2.32 (s, 3H), 2.25 (s, 3H).

The following alternate oxidizing reagents can be used in the N-oxidation: mCPBA; phthalic anhydride/urea.$H_2O_2$; $KMnO_4$; oxone; $O_3$; or a peracid.

NaOH can be used in the hydrolysis step to the acid instead of LiOH.

Instead of starting with the ethyl ester, 2,4-dimethyl nicotinic acid may be directly oxidized to the N-oxide too by using oxidants such as mCPBA; phthalic anhydride/urea.$H_2O_2$; $KMnO_4$; Oxone; $O_3$; or a peracid. A typical procedure: To 2,4-dimethyl nicotinic acid in 5× water was added 3 eq. of $K_2CO_3$. To the slurry, 1.1 eq. of oxone was added. The solid was filtered off. The filtrate was acidified

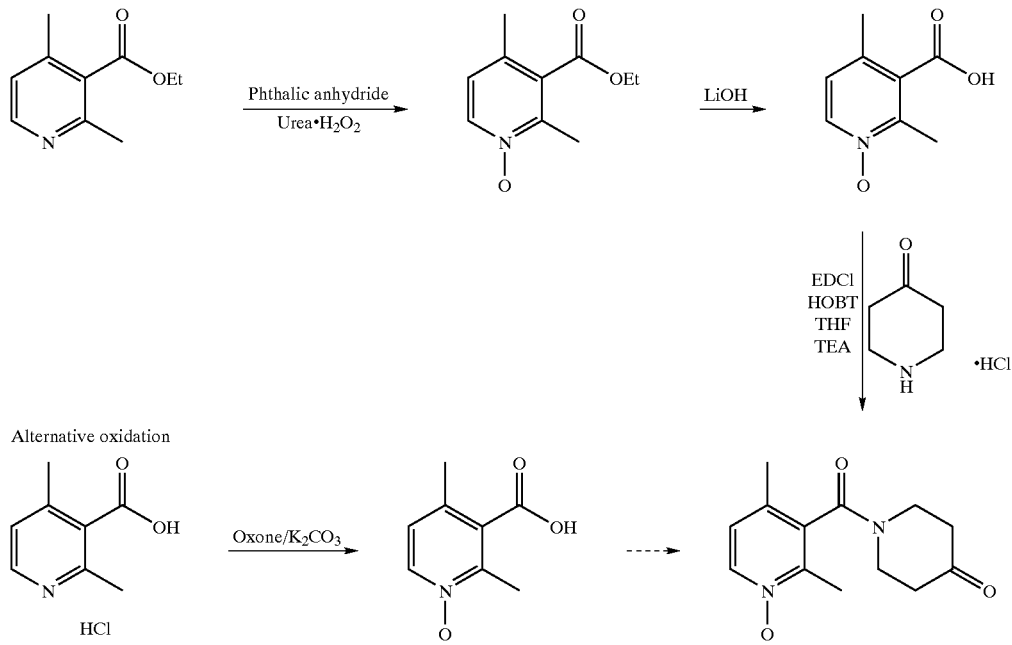

Alternative oxidation with HCl to pH about 1–2. The slurry was cooled to 0° C. for 1 hour. The final product was isolated by filtration.

Preparation of the Compound of Formula VII: To an agitated slurry of 100 g of 4-piperidone monohydrate hydrochloride salt, 120 g of 2,4-dimethyl nicotinic acid-N-oxide, 150 g of EDCl hydrochloride salt, and 26 g of HOBt in 500 mL of THF was added 225 mL of triethylamine. After addition, the mixture was heated to 50–55° C. for 3 hours, cooled to room temperature, and agitated overnight. After this period of time, the mixture was filtered. The wet cake was washed with 1L of hot THF four times. The THF washes were cooled to room temperature and filtered to give 106 g (65%) of the compound of formula VII as white solids.

$^1$H NMR (400 MHz, CDCl$_3$) δ 8.20 (d, J=6.8 Hz, 1H), 7.05 (d, J=6.8 Hz, 1H), 4.25–4.18 (m, 1H), 4.06–3.99 (m, 1H), 3.52 (m, 1H), 2.62 (m, 2H), 2.48 (s, 3H), 2.40 (m, 2H), and 2.28 (s, 3H).

Example 7

Preparation of the Compound of Formulas VI and V

The synthesis of these two compounds is described in pending provisional patent application, Ser. No. 60/329,562, filed Oct. 15, 2001. The following summarizes the details:

Preparation of the N-trifluoroacetate from isonipecotic Acid: To a suspension of 440 g of isonipecotic Acid in 1760 mL of isopropyl acetate at 0–10° C. was added 880 mL of trifluoroacetic anhydride over at least 2 h, while maintaining the temperature below 30° C. After complete addition, the reaction mixture was heated to 55–65° C. After about 2 h, the reaction mixture was cooled to about room temperature, and 1760 mL of isopropyl acetate was added. The reaction mixture was cooled to between –10° C. and 0° C., whereupon 1320 mL of water was added while maintaining the temperature below 15° C. This was followed by the addition of 1364 g of 25% sodium hydroxide solution while maintaining the temperature below 15° C. The biphasic mixture was stirred for about 3 h at room temperature. The aqueous layer was removed, and was extracted with 880 mL of isopropyl acetate. The combined isopropyl acetate solution was washed twice with 880 mL of a 15% sodium chloride solution each time. The reaction mixture was concentrated to about 1320 mL. Upon cooling, the product started to crystallize. The mixture was cooled to room temperature and 1760 mL of heptane was added. The suspension was cooled to between –5° C. and 5° C., stirred for 1 h, and then filtered. The collected solid was washed with 440 mL of heptane, and then dried under vacuum at 55–65° C. to give 613.6 g of the desired N-triluoroacetyl compound, mp: 113.5° C.

Preparation of the Acid Chloride, Followed by Friedel-Crafts Reaction: To a suspension containing 477 g of the N-trifluoroacetyl compound from the above step in 1900 mL of bromobenzene was added 257 g of thionyl chloride. The reaction mixture was heated to 60–65° C. over about 1 h. After another 1–2 h, the reaction mixture was cooled to 10–15° C., whereupon 588 g of aluminum chloride was added in 5 portions. During each addition, the temperature was maintained between 10–15° C. After the addition of aluminum chloride was complete, the reaction mixture was heated to 65–70° C. over a 3 h period. After about 1 h, another 70 g of aluminum chloride was added. After about 1 h, the reaction mixture was transferred to 2370 mL of a 6 N hydrochloric acid solution pre-cooled to between 5° C. and 10° C. During the transfer, the temperature was maintained below 40° C. The reaction flask was rinsed with 470 mL of bromobenzene and 470 mL of water. The biphasic mixture was separated. The organic solution was concentrated under reduced pressure to about 820 mL. To this mixture was added 1320 mL of methyl tert-butyl ether, and 1790 mL of heptane. After crystallization has started, another 860 mL of heptane was added. The suspension was cooled to between 0–5° C., stirred for at least 30 min, and the filtered. The collected solid was washed with 530 mL of cold heptane, dried under vacuum at 40–50° C. to give 537 g of the desired ketone compound, m.pt: 96.1° C.

Preparation of the Compound of Formula VI: A solution containing 293 g of the ketone compound from the above step, 336 g of 30% aqueous ethoxyamine solution, and 10 mL of acetic acid in 1170 mL of methanol was kept under reflux at about 65° C. for about 3 h. The reaction mixture was cooled to room temperature, and a solution of 577 mL of 25% sodium hydroxide was added. The biphasic mixture was vigorously stirred. After at least 10 min, the reaction mixture is added to a mixture of 1470 mL of water and 1470 mL of methyl tert-butyl ether. The layers were separated, and the organic layer was washed with 1470 mL of water, followed by 1470 mL of a 10% sodium chloride solution. The organic solution was concentrated to about 730 mL. The concentrate was diluted with 880 mL of methyl tert-butyl ether and concentrated again to about 730 mL. The distillation was repeated again with 880 mL of methyl tert-butyl ether, and the concentrate containing the compound of formula VI was used in the next step directly without additional purification.

Preparation of the Compound of Formula V from a Compound of Formula VI: Into a solution of the compound of Formula VI (600 mL of total solution including 247 g of active component in methyl tert-butyl ether as prepared in Example 3) was charged 758 mL of isopropyl alcohol ("IPA") and 2280 mL of methyl t-butyl ether ("MTBE"). An anhydrous IPA solution of HCl (4.8 N, 382 mL) was added dropwise. The resulting slurry was stirred for 12 h and then cooled to 0° C. After stirring 2 h, the crude product was filtered and washed with 200 mL of 1:2 of IPA and MTBE followed by 200 mL of MTBE. The resulting crude product was dried under vacuum at 55° C. for 2 days to give white solid (294 g, 92%). This crude product was found to contain 91:9 ratio of the E and Z-oximes respectively by HPLC analysis. The two isomers could be separated for analysis.

$^1$H NMR (400 MHz, DMSO-d6) major (Z-oxime): δ 8.99 (bs, 2H), 7.63 (d, J=8.4, 2H), 7.27 (d, J=8.4, 2H), 3.99 (q, J=7.0, 2H), 3.24–3.21 (m, 2H), 2.90–2.84 (m, 3H), 1.85–1.82 (m, 2H), 1.71–1.64 (m, 2H), 1.12 (t, J=7.0, 3H); minor (E-oxime): □7.60 (d, J=8.4), 7.44 (d, J=8.4), 4.13 (q, J=7.0), 1.25 (t, J=7.0).

Example 8

Preparation of the Compound of Formula VIII

The hydrochloride of formula V (10.0 g, 28.8 mmol) was free-based using ethyl acetate (100 mL) and 15% aqueous potassium carbonate (30 mL). The organic layer containing the free base of formula VI was washed with water (30 mL) and added to the compound of formula VII (7.5 g, 30 mmol). After 15 minutes of agitation, acetone cyanohydrin (2.9 g, 35 mmol) was added and the solution was warmed to reflux. The reaction mixture was concentrated via atmospheric distillation to 80 mL over an 8–10 hour period. The reaction was further distilled over a 4 hour period over which ethyl acetate saturated with water (100 mL) was added in regular portions during distillation. Additional acetone cyanohydrin (1.5 g, 17 mmol) was added and the resultant mixture was dried azeotropically with ethyl acetate. The reaction mixture was allowed to cool to 25° C. The solids were collected filtered, washed with ethyl acetate (20 mL) and dried in an oven to afford 13.7 g (84%) of the compound of formula VIII.

$^1$H NMR (400 MHz, CHCl$_3$, mixture of diastereomers) δ 8.2 (d, J=6.8 Hz, 1H), 7.5 (d, J=8.4 Hz, 2H), 7.1 (d, J=8.4 Hz, 2H), 7.0 (d, J=6.7 Hz, 1H), 4.6 (br, unresolved m, 1H), 4.0 (q, J=7.0 Hz, 2H), 3.4 (br, unresolved, m, 3H), 3.2 (m, 1H), 3.0 (m, 1H), 2.5 (m, 1H), 2.3 (s, 3H), 2.2 (br, unresolved, s and overlapping m, 6H), 2.1 (br, unresolved, m, 1H), 1.8 and 1.7 (br, unresolved, m, 5H), 1.2 (t, J=7.0 Hz, 3H);

$^{13}$C NMR (400 MHz, CHCl$_3$, mixture of diastereomers) δ 156.1, 158.3, 145.3, 139.9, 134.4, 133.1, 132.6, 130.9, 130.6, 129.0, 126.3, 124.6, 122.9, 117.7, 71.3, 69.9, 68.4, 60.5, 48.6, 47.3, 45.9, 44.2, 42.8, 42.3, 41.4, 41.0, 39.3, 37.8, 36.4, 36.0, 35.1, 34.7, 33.8, 33.4, 32.5, 31.3, 30.0, 28.7, 20.7, 19.4, 18.1, 16.9, 16.4, 16.1, 15.7, 15.1, 14.9, 14.4, 13.8, 13.2.

M.P. 207.6° C.

MS. Calcd for $C_{28}H_{34}BrN_5O_3$ 568, found 568.

Example 9

Preparation of the Compound of Formula I

Trimethylaluminum (20% in toluene, 50 mL) was slowly added to an agitated slurry of the compound of the formula VIII (10.0 g) in 50 mL of THF at −15° C. To this solution was then added methyl magnesium chloride in THF (3.0M, 8.9 g). The reaction was agitated at −5 to 0° C. for 24 hours, and quenched into aqueous sodium citrate (10 g in 100 ml of water) at 40–50° C. The organic layer was washed sequentially with 2.5% sodium hydroxide (50 ml, twice), a solution of 5.0 g of sodium citrate in 50 ml of water, and then of water (50 ml). The resulting solution was concentrated under vacuum to an oil (containing 9.27 g of active compound of formula I (94.3%). The title compound was crystallized from t-butylmethylether (50 ml) to afford 7.4 g (75%) of white solids.

$^1$H NMR (400 MHz, CDCl$_3$) δ 8.14 (d, J=6.8 Hz, 1H), 7.50 (d, J=8.1 Hz, 2H), 7.10 (m, 2H), 6.98 (d, J=6.8 Hz, 1H), 4.23–4.13 (m, 1H), 4.04 (m, 2H), 3.45–3.27 (m, 2H), 2.94 (m, 2H), 2.79 (m, 1H), 2.45 and 2.42 (2s, 3H), 2.42–2.36 (m, 1H), 2.25 and 2.21 (2s, 3H), 2.16–2.04 (m, 2H), 1.99 (m, 1H), 1.78 (m, 3H), 1.53 (m, 2H), 1.38 (m, 1H), 1.26–1.15 (m, 1H), 1.17 (m, 3H), and 0.91 (s, 3H).

Alternative Preparation of the Compound of Formula I:
Trimethylaluminum (20% in toluene, 17 mL, 2.0 eq) was slowly added to an agitated slurry of compound of formula VIII (10.0 g, 1.0 eq) in 20 mL of THF at −10° C. in flask A. In flask B, methyl magnesium chloride (3M in THF, 17 mL, 3.0 eq) was added to 30 mL THF cooled at 20–30° C. To this solution in flask B was added trimethylaluminum (20% in toluene, 17 mL, 2.0 eq). The solution in flask B was maintained at 35–40° C. The solution from flask B was added to the batch at −2 to 2° C. The batch was stirred for 6 hours and then quenched into aqueous sodium citrate (10 g in 100 mL of water) solution at 40–50° C. The organic layer was sequentially washed with 2.5% sodium hydroxide (50 mL) and then with water (50 mL). The resulting solution was concentrated under vacuum and contained 9 g of active compound of formula I.

2. Preparation of the Compound of Formula III:

Example 10

Preparation of the Compound of Formula X

The compound of formula X was prepared as disclosed in pending provisional patent application Ser. No. 60/368,707 filed of even date herewith. The details are summarized below in accordance with Scheme 3:

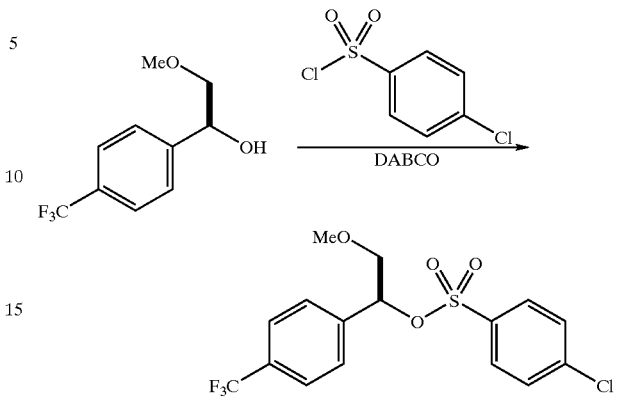

To a solution of the alcohol compound (300 g, prepared following the procedure described in Baroudy et al, WO 00/66558, published Nov. 9, 2000) and 1,4-diazabicyclo[2,2,2]octane ("DABCO", 214 g) in 1500 mL toluene was added a solution of 4-chlorobenzenesulfonyl chloride (345 g) in 1500 mL toluene at a temperature between −5 to −15° C. over 1 h. The reaction mixture was stirred at −5 to −15° C. for 1 h and quenched with water (1500 mL). The biphasic mixture was stirred at r.t. for 2 h, settled, and the aqueous layer split off. The organic layer was washed with 0.5 M sulfuric acid (1500 mL) followed by saturated sodium bicarbonate (1500 mL). The crude product was isolated by vacuum concentration. The crude material could be used directly in the following step. Alternatively, it could be recrystallized from toluene/heptane. The pure sulfonate product was isolated as pale yellow crystals (508.5 g, 94% yield, m.p.: 88.9° C.). $^1$H NMR (CDCl$_3$): 7.73 (m, 2H), 7.56 (d, J=8.3 Hz, 2H), 7.39 (m, 4H), 5.64 (dd, J$_1$=7.3, J$_2$=4.2, 1H), 3.73 (dd, , J$_1$=11.1, J$_2$=7.4, 1H), 3.60 (dd, , J$_1$=11.1, J$_2$=4.3, 1H), 3.31 (s, 3H).

Example 11

Preparation of the N-alkylated Product

The sulfonate from Example 10 and the N-Boc-protected piperazine compound (16.6 g) were

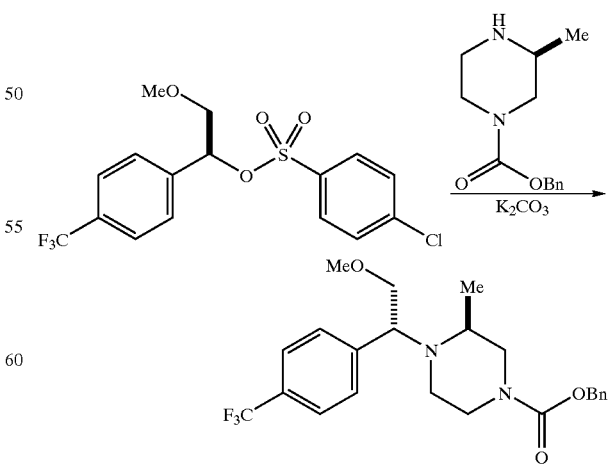

mixed in a mixture of toluene (40 mL) and acetonitrile (40 mL) containing extra-fine potassium carbonate (14.0 g).

This slurry was heated at 80–85° C. for 30 h and cooled. Solids were filtered and the filtrate was concentrated. HPLC analysis of the concentrate showed the presence of 18.7 g product (85% yield, RS/SS ratio: 95.9/4.1). The N-alkylated product was isolated as the HCl salt. $^1$H NMR (DMSO-d$_6$): 11.90, 11.51 (split br s, 1H), 8.07 (br s, 1H), 8.01(br d, J=6.6 Hz, 1H), 7.86 (br d, J=7.4 Hz, 2H), 7.37 (br m, 5H), 5.29, 4.69 (split br s, 1H), 5.11 (split br m, 2H), 3.00–4.30 (br m, 7H), 3.30 (s, 3H), 1.44, 1.36 (split br s, 3H).

Example 12

Preparation of the Compound of Formula X and its Tartrate

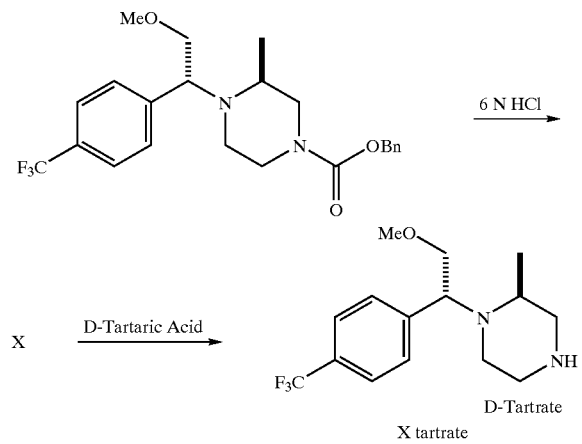

The product from Example 11 (18.7 g) was heated in 6 N HCl (60 mL) for 1 h at 95–100° C. and cooled. The resulting mixture was washed with toluene twice and basified with sodium hydroxide to pH>13. The basic mixture was extracted with toluene twice and back-washed with water once. The organic layer was concentrated to give an oil. HPLC analysis showed 12.8 g free base (99% yield) of the compound of Formula X. Pure free base (clear oil) was obtained after flash column chromatography. $^1$H NMR (CDCl$_3$): 7.58 (s, 4H), 4.16 (t, J=5.7 Hz, 1H), 3.80 (m, 2H), 3.38 (s, 3H), 3.00 (m, 2H), 2.78 (m, 1H), 2.64 (m, 2H), 2.46 (m, 1H), 2.31 (m, 1H), 1.73 (br s, 1H), 1.18 (d, J=6.3 Hz, 3H).

To a solution of D-tartaric acid (7.6 g) in 135 mL methanol was added the above free base in 35 mL toluene at 55–65° C. over 1 h. The resulting slurry was heated at 55–65° C. for 1 h and cooled slowly to 0° C. The solids were filtered, washed with isopropanol (70 ML), and dried at 50–55° C. under vacuum to yield the tartrate of the compound of Formula X. White solid (m.p.: 209.7° C., 17.7 g, 92% yield). $^1$H NMR (D$_2$O): 7.60 (d, J=8.2 Hz, 2H), 7.49 (d, J=8.2 Hz, 2H), 4.32 (s, 2H), 4.27 (t, J=5.8, 1H), 3.84 (m, 2H), 3.38 (m, 1H), 3.25 (dd, J$_1$=13 Hz, J$_2$=3.0 Hz, 1H), 3.20 (s, 3H), 3.09 (m, 1H), 2.86 (m, 3H), 2.68 (m, 1H), 1.21 (d, J=6.5 Hz, 3H).

Example 13

Preparation of the Compound of Formula XI

To a suspension of 100 g of pyrimidine-2,4-dimethyl-5-carboxylic acid (disclosed by T. Kress noted earlier), 111 g of 4-piperidone monohydrate hydrochloride, and 99 mL of N,N,N',N'-tetramethylethylenediamine (TMEDA) in 1L of acetonitrile at −10 to 0 C., 102 mL of methanesulfonyl chloride and 198 mL of TMEDA were added over a period of 6 hours. After the additions, the reaction mixture was agitated for 0.5 hour and filtered. Methanesulfonic acid was added to the filtrate to precipitate the excess TMEDA as its bis-salt. Acetonitrile was then displaced by isopropyl acetate via azeotrope distillation. After the solvent displacement, the mixture was filtered again. The filtrate was concentrated, cooled to 15 to 20 C. for crystallization. After filtration, the wet cake was dried under vacuum at 35–45 C. for 12 hours to give 99–115 g (65–75%) of the compound of formula XI as light yellow solids.

$^1$H NMR (400 MHz, CDCl$_3$) δ 9.02 (s, 1H), 4.16 (t, J=6.8 Hz, 2H), 3.55 (t, J=6.8 Hz, 2H), 2.66 (t, J=6.8 Hz, 2H), 2.52 (s, 6H), and 2.45 (t, J=6.8 Hz, 2H).

Example 14

Preparation of the Compound of Formula XII from the Compounds of Formulas X and XI Using Acetone cyanohydrin: To a slurry of 50 g (0.11 mol) of the tartrate of the compound of formula X (from Example 12) in 500 mL of EtOAc, a solution of 15 g of K$_2$CO$_3$ in 150 mL of water was added. The solution was stirred at 30–40° C. for 30 minutes. The layers were separated. The organic layer was washed with a solution of 15 g of K$_2$CO$_3$ in 150 mL of water, followed by 150 mL of water. The organic layer was azeotropically dried at 75–82° C. The resulting solution was added more EtOAc to reach 700 mL volume. Then 27 g (0.1155 mol) of the compound of formula XI (from Example 13) was added, followed by 10 mL (0.11 mol) of acetone cyanohydrin. The solution was slowly distilled off EtOAc at a rate of 1 mL/min for 6 hours. More acetone cyanohydrin (5 mL, 0.055 mol) was added. The solution was again slowly distilled off EtOAc at a rate of 1 mL/min for 4 hours. The solution was concentrated at 80–90° C. to 80 mL of volume. EtOAc (50 mL) was added at 800 C. followed by 200 mL of Heptane. After seeding at 80° C., the solution was slowly cooled to room temperature and stirred for 12 hours. The solid was filtered to give 52.5 g (87% yield) of the desired compound of formula XII.

Using NaCN/HOAc: To a slurry of 20 g (44 mmol) of the tartrate of the compound of formula X (from Example 12) in 160 mL of iPrOAc, a solution of 12 g of K$_2$CO$_3$ in 120 mL of water was added. The solution was stirred at 30–40° C. for 30 minutes. The layers were separated. The organic layer was washed with 120 mL of water. The organic layer was azeotropically dried at 80–90° C. Then 10.8 g (46 mmol) of the compound of formula XI was added, followed by 3.2 g (66 mmol) of NaCN. After charging 3.8 mL (46 mmol) of HOAc, the slurry was heated to 70° C. and stirred for 1 hour. The temperature was raised to 90° C. and stirred for another 2 hours. After cooling to room temperature, a solution of 5 g of K$_2$CO$_3$ in 50 mL of water was added. The solution was stirred for 10 minutes. The layers were separated, and organic layer was azeotropically dried under vacuum to a volume of 25 mL. The solution was heated to reflux and 20 mL of iPrOAc was added, followed by 100 mL of Heptane. The slurry was cooled to room temperature for 5 hours, followed by 0° C. for 2 hours. The solid was filtered to give 21.4 g (91% yield) of the desired compound of formula XII.

Example 15

Preparation of the Compound of Formula III from the Compound of Formula XII

To a solution of 85 g (156 mmol) of compound of formula XII in 425 mL of THF at 15–20° C., 164 mL (328 mmol) of AlMe₃ (2.0M in Toluene) was added, followed by 151 mL (452 mmol) of MeMgCl (3.0 M in THF) at a temperature between 20–30° C. The slurry was stirred at 20–30° C. for 2 hours, and was quenched by transferring into a solution of 51 g of sodium citrate in 510 mL of water at a temperature between 35–45° C. The layers were separated and organic layer was washed with 250 mL of 5% NaOH twice. The organic layer was azeotropically dried under vacuum to give an oil containing 79 g of active compound of formula III (95% yield).

The compounds of formulas I and III may be converted to the respective acid salts of formulas II and IV by reacting with a suitable acid, if so desired. Such techniques are well known to those skilled in the art and are also described in pending provisional patent applications, Ser. Nos. 60/334,330 and 60/334,331, both filed Nov. 29, 2001. They may also be formulated into suitable pharmaceutical compositions using techniques well known to those skilled in the art, as well as the techniques described in the afore-mentioned WO 00/66559 and WO 00/66558.

It will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A process to prepare a piperazine of the formula III:

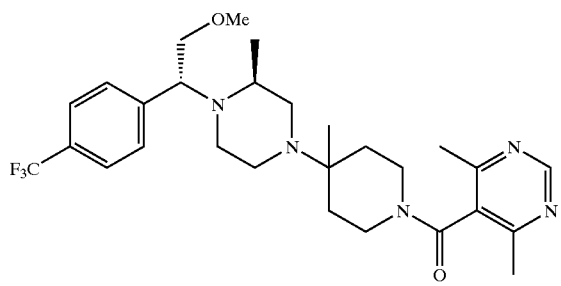

III said process comprising:

(a) reacting a compound of formula X

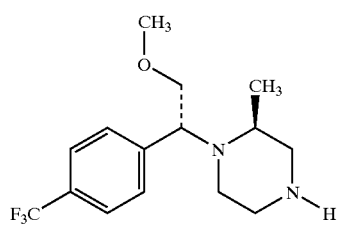

X with a compound of formula XI:

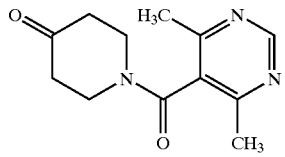

XI and a cyanating compound, to form the compound of formula XII:

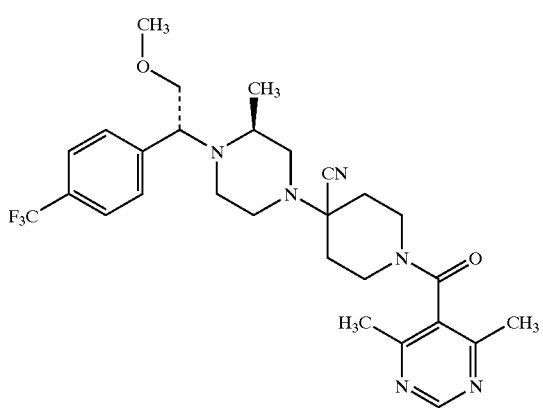

XII and (b) reacting said compound of formula XII with a methyl-metal and an organometallic reagent to yield the compound of formula III.

2. The process of claim 1, wherein said cyanating compound in step (a) is selected from the group consisting of HCN; acetone cyanohydrin; cyclohexanone cyanohydrin; a mixture of (C₂H₅)₂AlCN and Ti(OPr)₄, a mixture of acetic acid, H₂SO₄; NaHSO₄, KHSO₃ or Na₂S₂O₅ with NaCN or KCN; NaCN and acid; KCN and acid; trimethylsilylcyanide; glycolonitrile; mandelonitrile; glycinonitrile; acetone amino nitrite; dimethylaminoacetonitrile; and mixtures thereof.

3. The process of claim 2, wherein said cyanating compound is acetone cyanohydrin or a mixture of sodium cyanide and acetic acid.

4. The process of claim 1, wherein step (a) contains a solvent, said solvent being an ester, nitrile, ether, hydrocarbon or mixtures thereof.

5. The process of claim 4, wherein said solvent is ethyl acetate isopropyl acetate.

6. The process of claim 1, wherein said organometallic reagent in step (b) is selected from the group consisting of trimethylaluminum, triethylaluminum, triethylborane, methyl zinc and tetramethyl tin.

7. The process of claim 6, wherein said organometallic reagent is trimethylaluminum.

8. The process of claim 1, wherein said step (b) is performed in a solvent, said solvent being an ether, hydrocarbon or mixtures thereof.

9. The process of claim 1, wherein said compound of formula III is further reacted with an acid to form an acid salt of the formula IV:

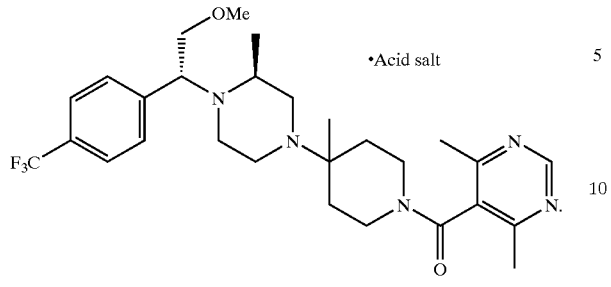

IV ·Acid salt

10. The process of claim 1, wherein said compound of formula XI is prepared by a process comprising condensing pyrimidine-2,4-dimethyl-5-carboxylic acid and 4-piperidone monohydrate hydrochloride in the presence of a base and an acid halide in a solvent.

11. The process of claim 10, wherein said base is N,N,N',N'-tetramethyl ethylenediamine, said acid halide is methane sulfonyl chloride and said solvent is acetonitrile.

12. The process at claim 1, wherein said methyl-metal in step (b) is selected from the group consisting of methyl magnesium chloride, methyl magnesium bromide, methyl magnesium iodide and methyl lithium.

13. The process of claim 12, wherein said methyl-metal is methyl magnesium chloride.

14. A compound of the formula:

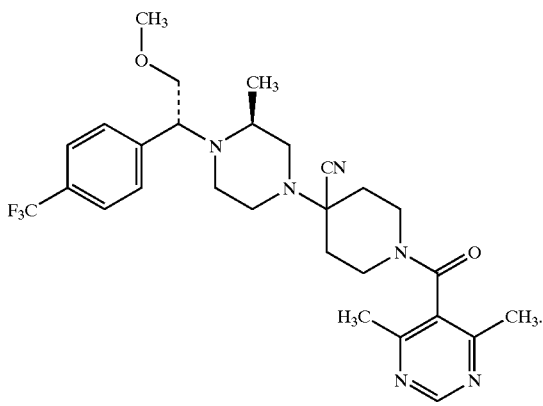

* * * * *

UNITED STATES PATENT AND TRADEMARK OFFICE
CERTIFICATE OF CORRECTION

PATENT NO. : 6,992,189 B2
APPLICATION NO. : 10/401070
DATED : January 31, 2006
INVENTOR(S) : William Leong et al.

Page 1 of 1

It is certified that error appears in the above-identified patent and that said Letters Patent is hereby corrected as shown below:

In the Claims:

Claim 2, col. 26, line 41, please correct "mixture of" to:
-- mixture of: --

Claim 2, col. 26, line 42, please correct "$Na_2S_2O_5$ with" to:
-- $Na_2S_2O_5$; with --

Claim 2, col. 26, line 45, please correct "nitrite" to:
-- nitrile --

Claim 5, col. 26, line 53, please correct "acetate isopropyl" to:
-- acetate or isopropyl --

Claim 10, col. 27, line 19, please correct "an acid" to:
-- a sulfonic acid --

Claim 11, col. 27, line 21, please correct "said acid" to:
-- said sulfonic acid --

Signed and Sealed this

Twenty-second Day of December, 2009

David J. Kappos
*Director of the United States Patent and Trademark Office*